US012663366B2

(12) United States Patent
Ciccone et al.

(10) Patent No.: US 12,663,366 B2
(45) Date of Patent: Jun. 23, 2026

(54) SYSTEMS AND METHODS FOR AN OPEN PATH GAS DETECTOR WITH AN INTEGRATED OPTICAL SENSOR

(71) Applicant: MSA Technology, LLC, Cranberry Township, PA (US)

(72) Inventors: Nicholas Emidio Ciccone, Allison Park, PA (US); Nils von Hemm, Berlin (CH); Gavin Bai, Mars, PA (US); Henry A. Fonzi, III, Mars, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 168 days.

(21) Appl. No.: 18/473,419

(22) Filed: Sep. 25, 2023

(65) Prior Publication Data

US 2025/0102424 A1     Mar. 27, 2025

(51) Int. Cl.
*G01N 21/31* (2006.01)
*G01N 21/3504* (2014.01)
(Continued)

(52) U.S. Cl.
CPC ......... *G01N 21/31* (2013.01); *G01N 21/3504* (2013.01); *G01N 33/0027* (2013.01);
(Continued)

(58) Field of Classification Search
CPC .............. G01N 21/31; G01N 21/3504; G01N 33/0027; G01N 2021/3513;
(Continued)

(56) References Cited

U.S. PATENT DOCUMENTS

| | | | | |
|---|---|---|---|---|
| 4,924,095 A | * | 5/1990 | Swanson, Jr. ...... | G01N 21/3504 |
| | | | | 250/338.5 |
| 10,161,866 B2 | * | 12/2018 | Knox ..................... | G08B 25/10 |

(Continued)

FOREIGN PATENT DOCUMENTS

| | | | | |
|---|---|---|---|---|
| CN | 203479672 U | * | 3/2014 | ............. G01N 15/06 |
| EP | 1300816 A1 | * | 4/2023 | ........... G08B 17/125 |

OTHER PUBLICATIONS

Patent Cooperation Treaty, PCT/US2024/047368, International Search Report and Written Opinion of the International Searching Authority, Jan. 31, 2025.
(Continued)

*Primary Examiner* — Michelle M Iacoletti
*Assistant Examiner* — Noah J. Haney
(74) *Attorney, Agent, or Firm* — Jones Day

(57) ABSTRACT

Systems and methods are provided for an open path gas detection system having a receiver with an optical sensor configured to continuously capture optical image data. The field of view of the optical sensor can include the path of a beam of focused light received by a light sensor of the receiver. The receiver can be configured to receive and temporarily store the optical image data in a memory buffer, and then transfer the optical image data to a persistent memory area upon receipt of a transfer command. A transfer command may be provided in various situations, such as when requested by a receiver, when a predefined object of interest is identified in the optical image data, or when a blockage occurs and light sensor is no longer receiving the beam of focused light.

18 Claims, 10 Drawing Sheets

(51) Int. Cl.

| | | |
|---|---|---|
| *G01N 33/00* | (2006.01) | |
| *G06V 20/40* | (2022.01) | |
| *G06V 20/52* | (2022.01) | |

(52) U.S. Cl.
CPC .............. *G06V 20/44* (2022.01); *G06V 20/52* (2022.01); *G01N 2021/3513* (2013.01)

(58) Field of Classification Search
CPC ........... G01N 33/0004; G01N 33/0009; G01N 33/0031; G01N 33/007; G06V 20/44; G06V 20/52
USPC ................................................. 356/300–334
See application file for complete search history.

(56) References Cited

U.S. PATENT DOCUMENTS

| | | | |
|---|---|---|---|
| 10,748,401 B2 | 8/2020 | Oertel et al. | |
| 11,108,995 B2 | 8/2021 | Wilson, Jr. | |
| 2005/0225569 A1* | 10/2005 | Kim ..................... | H04N 13/261 348/E13.02 |
| 2006/0238741 A1 | 10/2006 | Ninomiya et al. | |
| 2007/0132773 A1 | 6/2007 | Plante | |
| 2007/0291128 A1* | 12/2007 | Wang ..................... | H04N 7/185 901/1 |
| 2013/0116883 A1* | 5/2013 | Kormann ............. | A01B 79/005 701/32.3 |
| 2017/0131202 A1* | 5/2017 | McClintock ........... | H04N 7/183 |
| 2017/0336281 A1 | 11/2017 | Waxman et al. | |
| 2019/0026564 A1* | 1/2019 | Lau ......................... | H04N 23/61 |
| 2019/0113414 A1* | 4/2019 | Tsuzuki .................. | G01M 3/04 |
| 2019/0137388 A1* | 5/2019 | Mallery ................ | G01J 5/0806 |
| 2019/0302013 A1 | 10/2019 | Wang | |
| 2020/0264149 A1 | 8/2020 | Kester et al. | |
| 2021/0156741 A1* | 5/2021 | Rhead .................... | G01J 5/0846 |
| 2021/0190747 A1* | 6/2021 | Cobley ............. | G01N 33/0022 |
| 2021/0287524 A1* | 9/2021 | Hermann ............. | G08B 17/125 |

OTHER PUBLICATIONS

DET-TRONICS; xWatch Explosion-Proof Camera with X-Series Flame Detectors, Addendum; Product Brochure; 2015.

Dräger; Dräger Flame 5000 Flame Detection; Product Brochure.

Fire & Gas Detection Technologies, Inc.; FlameSpec UV-IR-HD, UV/IR Flame Detector; Product Brochure.

Fire & Gas Detection Technologies, Inc.; Triple IR (IR3) Flame Detector; Product Brochure.

* cited by examiner

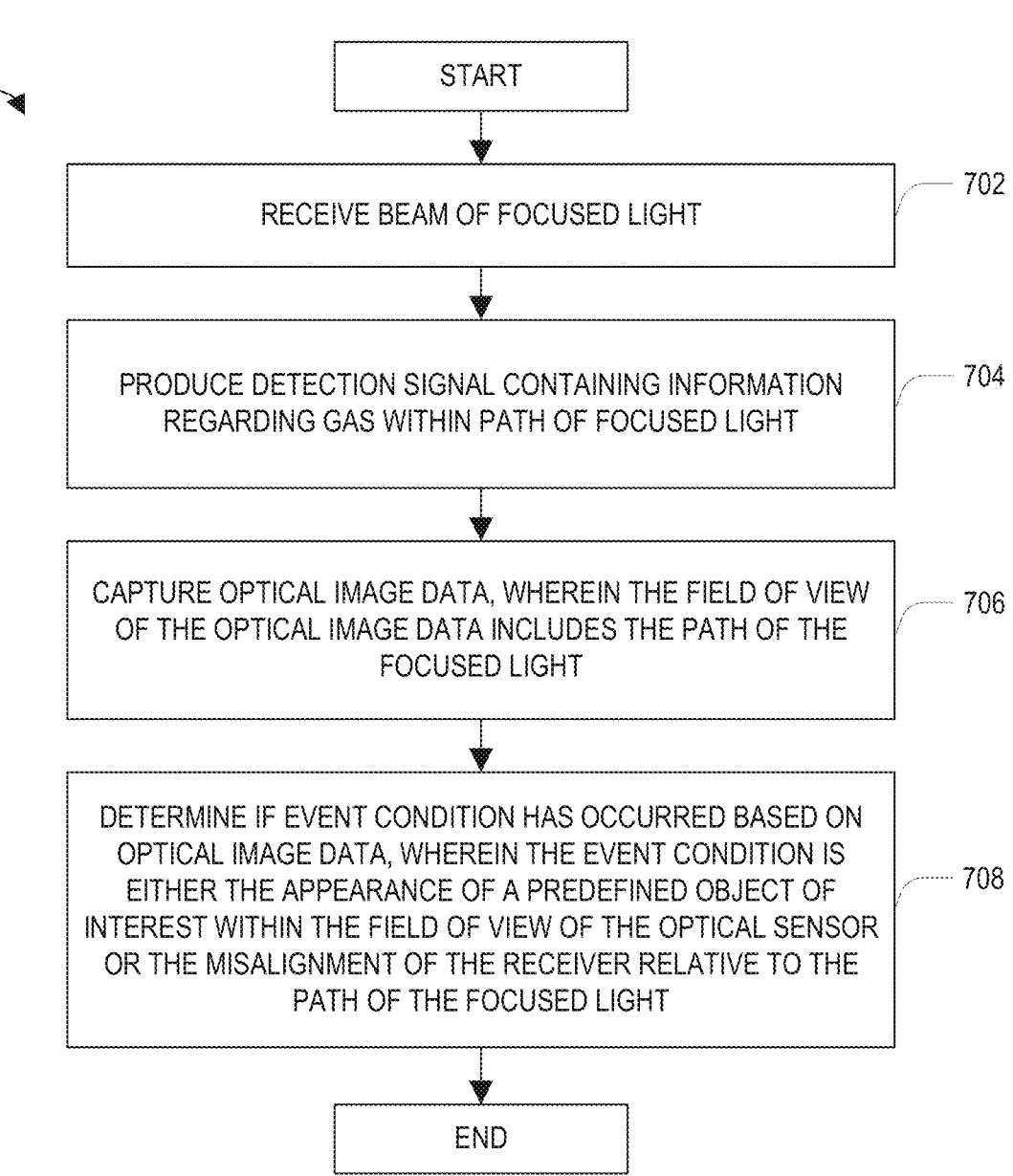

700

START

RECEIVE BEAM OF FOCUSED LIGHT — 702

PRODUCE DETECTION SIGNAL CONTAINING INFORMATION REGARDING GAS WITHIN PATH OF FOCUSED LIGHT — 704

CAPTURE OPTICAL IMAGE DATA, WHEREIN THE FIELD OF VIEW OF THE OPTICAL IMAGE DATA INCLUDES THE PATH OF THE FOCUSED LIGHT — 706

DETERMINE IF EVENT CONDITION HAS OCCURRED BASED ON OPTICAL IMAGE DATA, WHEREIN THE EVENT CONDITION IS EITHER THE APPEARANCE OF A PREDEFINED OBJECT OF INTEREST WITHIN THE FIELD OF VIEW OF THE OPTICAL SENSOR OR THE MISALIGNMENT OF THE RECEIVER RELATIVE TO THE PATH OF THE FOCUSED LIGHT — 708

END

FIG. 7

SYSTEMS AND METHODS FOR AN OPEN PATH GAS DETECTOR WITH AN INTEGRATED OPTICAL SENSOR

BACKGROUND

Gas detectors are instruments designed to detect the presence of gasses (e.g., hazardous gasses and vapors) in various settings. These detectors may be useful in providing data regarding current conditions as well as safety alarms, indicating dangerous conditions may be present. False alarms could result in unnecessary actions, such as evacuations or other remedial actions, which could result in unnecessary expenditures of time, effort, and money.

SUMMARY

Systems and methods are provided herein for open path gas detectors having a receiver with an integrated optical sensor. The optical sensor may provide optical image data that may be used to determine if event conditions have occurred (e.g., misalignment of the transmitter and the receiver, the presence of a known object of interest near the path of the light beam, weather, etc.) that may have an effect on the focused light beam received by the receiver. The receiver may be configured to continuously capture and store the optical image data in a temporary memory location, and then to transfer the optical image data to a persistent memory location upon receipt of a transfer command, which may be provided when an event condition is determined to occur. A determination of whether an event condition has occurred may be made by the receiver based on the detection signal (i.e., the light intensity at the receiver) and/or the optical image data, using, for example, an object recognition model. In this manner, the open path gas detector may better control the capture and storage of the optical image data, and may provide improved information to a user (e.g., objects identified in the optical image data, etc.) that may allow a user receiving the information to better react to an event that is altering or has the potential to alter the detection signal of the open path gas detector.

In one aspect, the present disclosure provides a gas detection system. The system may include a receiver. The receiver may include a light sensor configured to receive a beam of focused light generated by a transmitter and to produce a detection signal containing information regarding the gas within the path of the focused light, an optical sensor configured to continuously capture optical image data, wherein the field of view of the optical sensor includes the path of the beam of focused light, and an electronic assembly including a memory buffer and a persistent memory area. The memory buffer may be configured to receive and temporarily store the optical image data and transfer the optical image data to the persistent memory area upon receipt of a transfer command.

In another aspect, the present disclosure provides a gas detection system. The system may include a receiver. The receiver may include a light sensor configured to receive a beam of focused light generated by a transmitter and to produce a detection signal containing information regarding the gas within the path of the focused light, an optical sensor configured to capture optical image data, wherein the field of view of the optical sensor includes the path of the focused light, and an electronic assembly including a processor. The processor may be configured to receive the optical image data and determine if an event condition has occurred based on the optical image data.

In yet another aspect, the present disclosure provides a method of gas detection. The method may include receiving a beam of focused light, producing a detection signal based on the received focused light, the detection signal containing information regarding the gas within the path of the focused light, capturing optical image data, wherein the field of view of the optical image data includes the path of the focused light, and determining if an event condition has occurred based on the optical image data, wherein the event condition is the appearance of a predefined object of interest within the field of view of the optical sensor.

In still another aspect, the present disclosure provides a gas detection system. The system may include a transmitter configured to produce a beam of focused light along a path and a receiver including a light sensor configured to receive the beam of focused light and to produce a detection signal containing information regarding the gas within the path of the focused light. At least one of the transmitter and the receiver may include an optical sensor configured to capture optical image data, wherein the field of view of the optical sensor may include the path of the focused light, and an electronic assembly including a processor configured to receive the optical image data and determine if an event condition has occurred based on the optical image data.

BRIEF DESCRIPTION OF DRAWINGS

FIG. 7 is a flowchart diagram of an example method of gas detection using a receiver with an integrated optical sensor

DETAILED DESCRIPTION

Figure 1A:
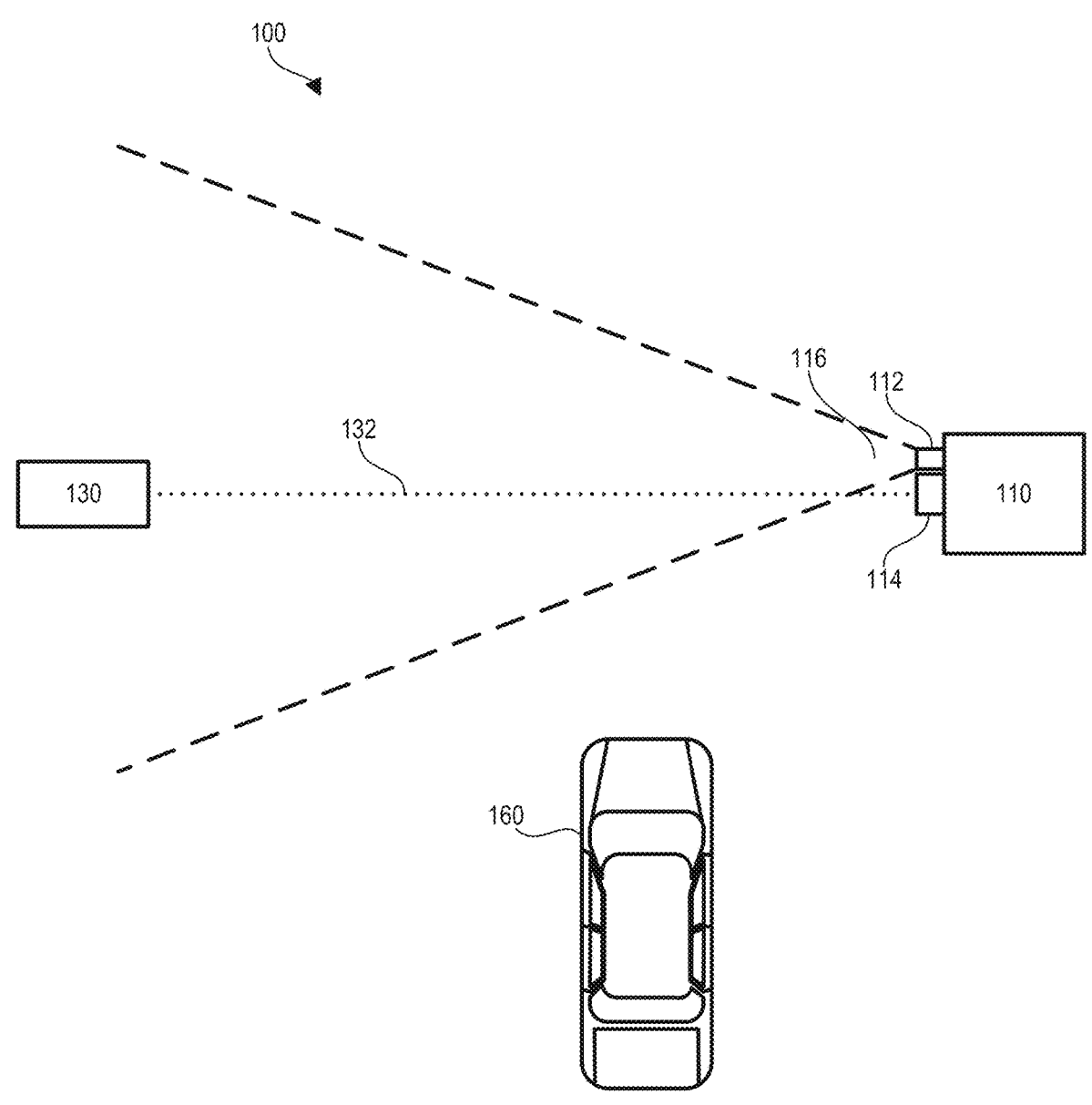
FIG. 1A is an illustration depicting an arrangement of an open path gas detector with a receiver having an integrated optical sensor.

Gas detectors, including open path gas detectors, are instruments designed to detect the presence of hazardous gasses and vapors in various settings, including in industrial, environmental, and safety applications. Unlike single-point gas detectors that are stationed at fixed locations, in some embodiments, open path gas detectors offer a more expansive coverage by utilizing a beam of electromagnetic radiation (e.g., infrared light) to monitor vapor and gas concentrations along a designated path of interest. Accordingly, one of the advantages of open path gas detectors is their ability to monitor large areas, making them well-suited for outdoor and open environments.

Open path gas detection systems may rely on two components: a transmitter and a receiver, which are positioned at a distance from each other. The transmitter may be configured to emit a beam of focused light, which may include one or more specific wavelengths that correspond to the absorption bands of the gases being targeted for detection. Accordingly, as the emitted light beam travels through the air, gases present in its path can absorb specific wavelengths of light. As a result, the intensity of the light being measured by the receiver may decrease. By quantifying the reduction in light intensity, the receiver can determine the concentration of the gases present along the path of the focused light beam.

Given their quick response times and ability to detect a wide range of gases, including toxic, flammable, and explosive substances, open path gas detectors are useful in several industries, such as oil and gas, chemical manufacturing, and environmental monitoring. Since these devices are often relied on for both safety and the early detection of gas leaks, regular calibration and maintenance may be required to uphold the accuracy and reliability of these devices.

Because open path gas detectors can provide large coverage areas, they may be installed in remote locations, some of which may not be immediately accessible by an operator. For instance, both the transmitter and the receiver may be several miles away from the operators monitoring the devices (e.g., in an offshore oil rig). Consequently, whenever an abnormal condition is detected, whether it be misalignment, blockage of the focused light beam, a general system fault, or an actual gas leak, it may take a significant amount of time before an operator is actually able to reach the site and determine what caused the abnormal condition. Further complicating the situation, during the time it takes an operator to travel to the detector, the condition of the open path gas detector system can change. For example, if a bird lands in front of the receiver and blocks the received light from the transmitter, a fault condition may be provided to the operator who may send a technician to investigate, but by the time the technician physically gets to the system, the bird may have flown away and the system's condition may accordingly have been restored to normal operation. In such a scenario, the technician may be left to guess as to what may have caused the fault condition.

In order to address these deficiencies, among others, the present disclosure provides, in part, systems and methods that utilize a receiver with an optical sensor that can produce optical image data (e.g., video) that may be selectively stored and provided to a user (e.g., an operator). This image recording capability may provide a visual record to users of the environment in front of the receiver, thereby enabling them to diagnose abnormal conditions quickly and remotely. This may, for example, eliminate the need to send a technician out to the device to diagnose an issue that may clear itself by the time they would get to it. For instance, if the optical image data shows that it is likely a temporary condition (e.g., a bird sitting in front of the receiver), then a user may know not to travel to the site. However, if the imagery shows a more permanent condition, such as a vehicle parked in the transmitter pathway or a misalignment, then the user may know to take an informed corrective action much sooner.

Relatedly, in some aspects, the optical image data may be processed and predefined objects of interest may be determined, which can be provided as information to a user. For example, the optical image data may determine that a bird entered the field of view of the optical sensor, and this information may be provided to a user, thereby allowing them to avoid actually reviewing the optical image data in some instances. In other aspects, the optical image data may be continuously produced by the optical sensor, stored in a temporary memory, and only then transferred to another memory area upon receiving a transfer command. This arrangement may allow for a user to access optical image data from prior to an event condition. For instance, if a truck parks in front of the sensor, the current optical image data simply show the white side of the truck (i.e., it may be unclear as to what is causing the blockage), but upon reviewing the past optical image data, it may be determined that a truck drove into the field of view and blocked the path of the light beam. These aspects, as well as others, are described in further detail below with reference to the drawings.

FIG. 1A is an illustration depicting an arrangement of an open path gas detector 100 with a receiver 110 having an integrated optical sensor 112. A transmitter 130 is shown positioned at a distance from the receiver 110. The transmitter 130 may be configured to emit a beam of focused light 132 (e.g., infrared light) in the direction of the receiver 110. A light sensor 114 may be integrated with the receiver 110, and configured to receive the beam of focused light 132 and to produce a detection signal containing information related to the gas or vapors within the path of the focused light 132. In this manner, the air properties in the area between the receiver 110 and the transmitter 130 may be monitored.

The optical sensor 112 may be configured to capture optical image data (e.g., images, video, etc.), and the optical image data may be specifically captured continuously when in operation. The field of view 116 of the optical sensor 112 may include, at least, a substantial portion of the path of the focused light 132. In some aspects, the field of view 116 may include the majority of the path of the focused light 132 or even the entire path of the focused light 132. For instance, the optical sensor 112 may include the transmitter 130 within its field of view 116. As will be further described, the optical image data may be stored and accessed by a user (e.g., operator), who may rely on optical image data to make safety and maintenance decisions for the open path gas detector 100. In some aspects, the optical image data may be continuously stored, at least for a period of time, which may allow a user to access optical image data prior to a fault condition or signal change in the detection signal. In this depiction, an object of interest 160 (i.e., a vehicle) is shown outside of the field of view 116 of the optical sensor 112.

Although the receiver 110 and transmitter 130 are not drawn to scale or depicted in the context of a worksite, it should be readily appreciated that these two components may be positioned at any suitable position from one another and attached or connected to any suitable structure (e.g., building, platform, post, etc.). The transmitter 130 may be positioned to provide the focused light 132 directly to the light sensor 114 of the receiver 110, and may rely on various known transmitter techniques, depending on the sensor application. For instance, the transmitter 130 may provide the focused light 132 in a continuous or patterned manner, and at an intensity tailored to the specific arrangement of the open path gas detector 100. Depending on the target gases or vapors to be measured, the focused light 132 may include one or more specific wavelengths known to effectively interact with the target species to be monitored.

Figure 1B:
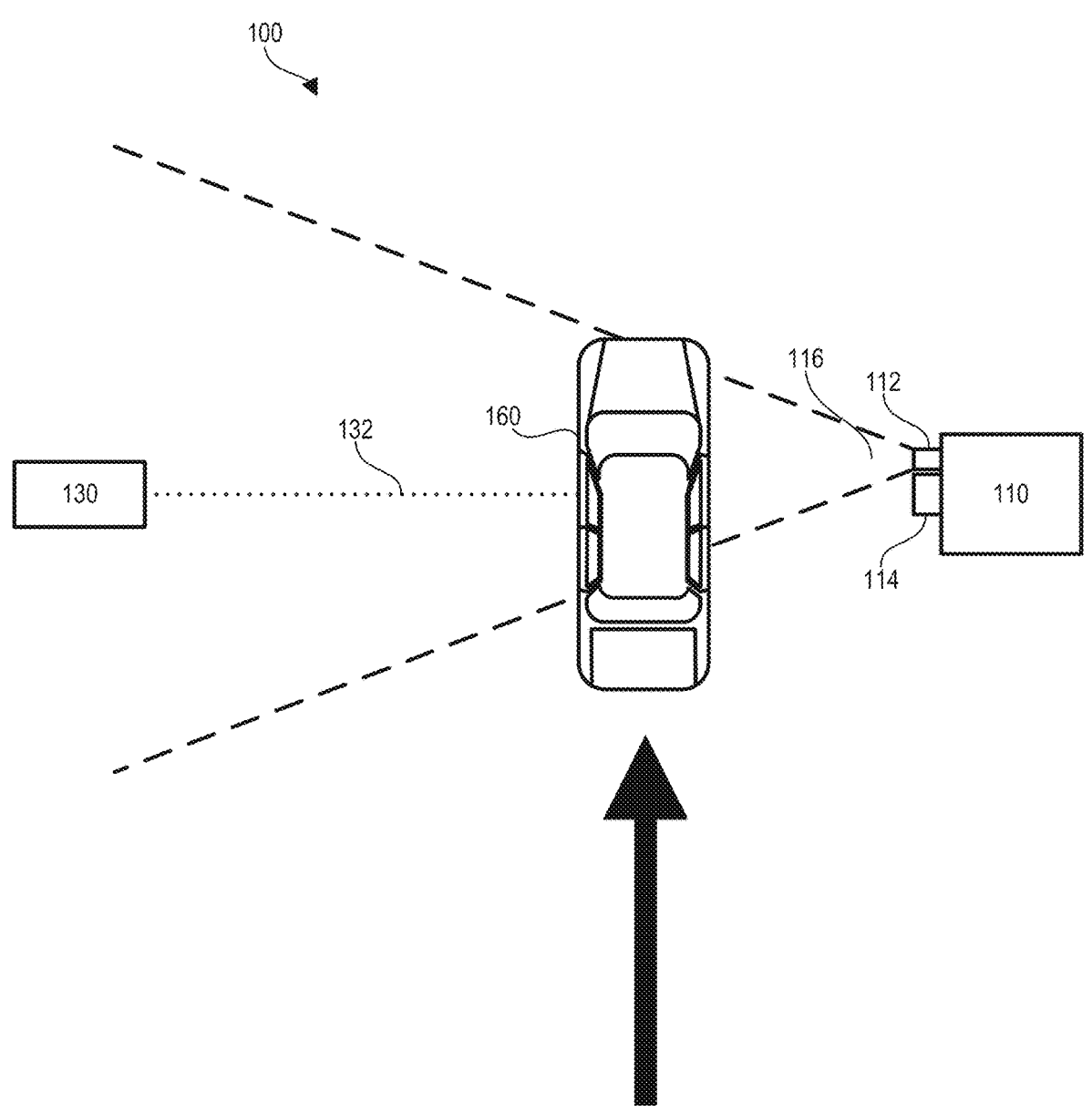
FIG. 1B is an illustration depicting the open path gas detector arrangement of FIG. 1A with an object of interest having entered the field of view of the optical sensor.

FIG. 1B depicts the open path gas detector 100 of FIG. 1A with the object of interest 160 now having entered the field of view 116 of the optical sensor 112 As shown, the object of interest now blocks the focused light 132 from reaching the light sensor 114. Without the optical sensor 112, it would be challenging for a user reviewing the output information from the receiver 110 to know why the detection signal produced by the light sensor 114 would be suddenly reading a fault condition. As previously described, since there are a number of conditions that all produce a similar loss of signal (e.g., misalignment of the transmitter 130 and receiver 110, loss of power to the transmitter 130, a defective light sensor 114, etc.), travel by a technician to the site to manually determine the cause of the fault condition would otherwise be required. The inclusion of the integrated optical sensor 112 into the receiver 110 allows a user to instead simply review the optical image data and determine that an object of interest 160 had entered pathway of the focused light 132, which may allow for a different corrective action to be employed (e.g., placing a call and instructing an operator to move a parked vehicle).

As will be further described, in some aspects, the receiver 110 may be configured to provide information to a user that goes beyond a simple photo taken upon interruption of or a change to the detection signal produced by the light sensor 114. For instance, the optical sensor 112 may be configured to continuously acquire the optical image data, which may be stored for at least an appreciable amount of time (e.g., 1 minute). This arrangement may allow optical image data from prior to a change in the detection signal to be accessed, which can help a user better determine the cause of the incident. Additionally, because the optical image data may be continuously analyzed to determine various event conditions, such as the misalignment of the transmitter 130 or a known object of interest entering the field of view 116, this additional information can be provided to a user, further improving their ability to ensure that the open path gas detector 100 operates as intended.

Figure 2A:
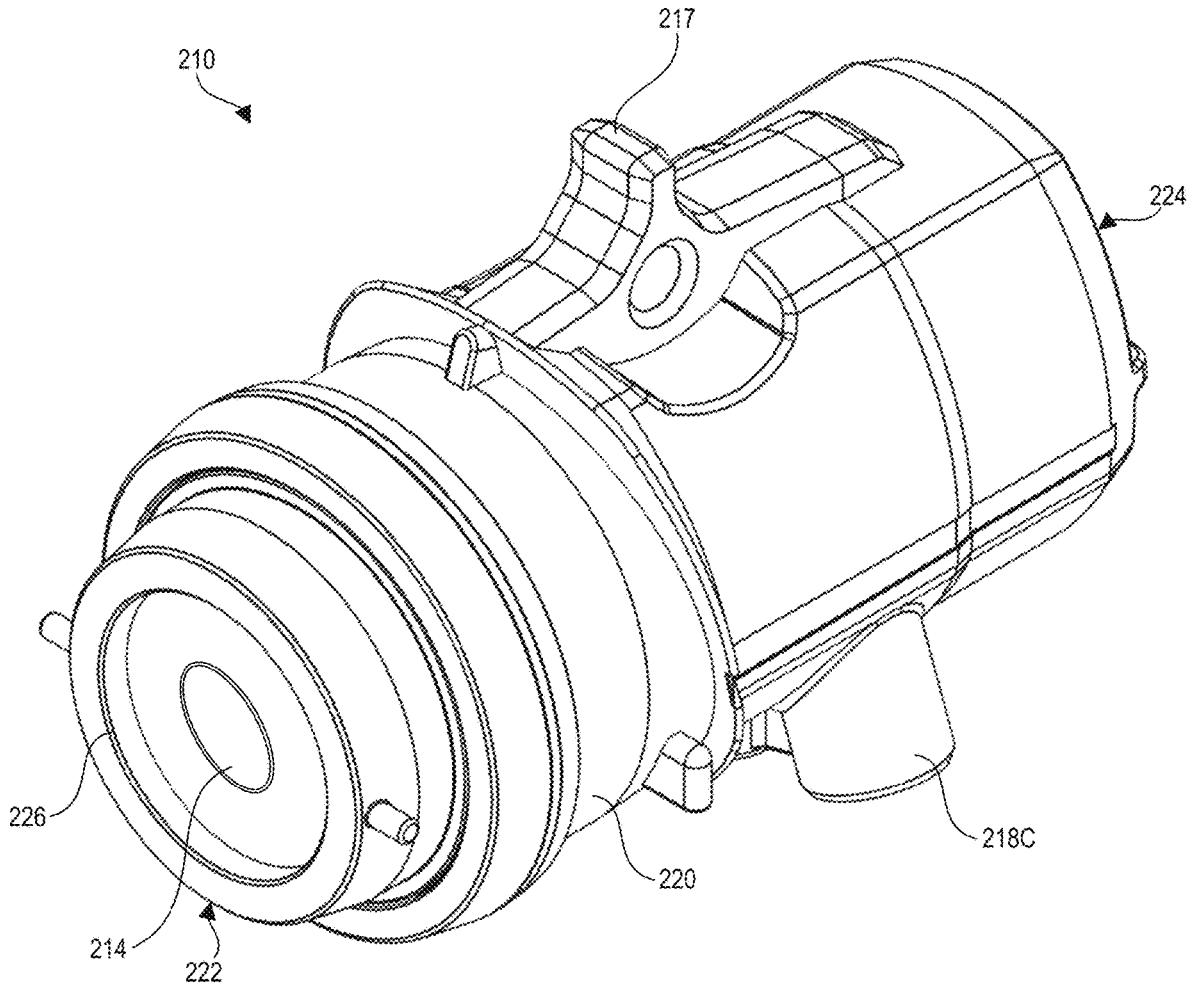
FIG. 2A is an illustration depicting a top perspective view of a receiver with an integrated optical sensor to be used in an open path gas detection system.
Figure 2B:
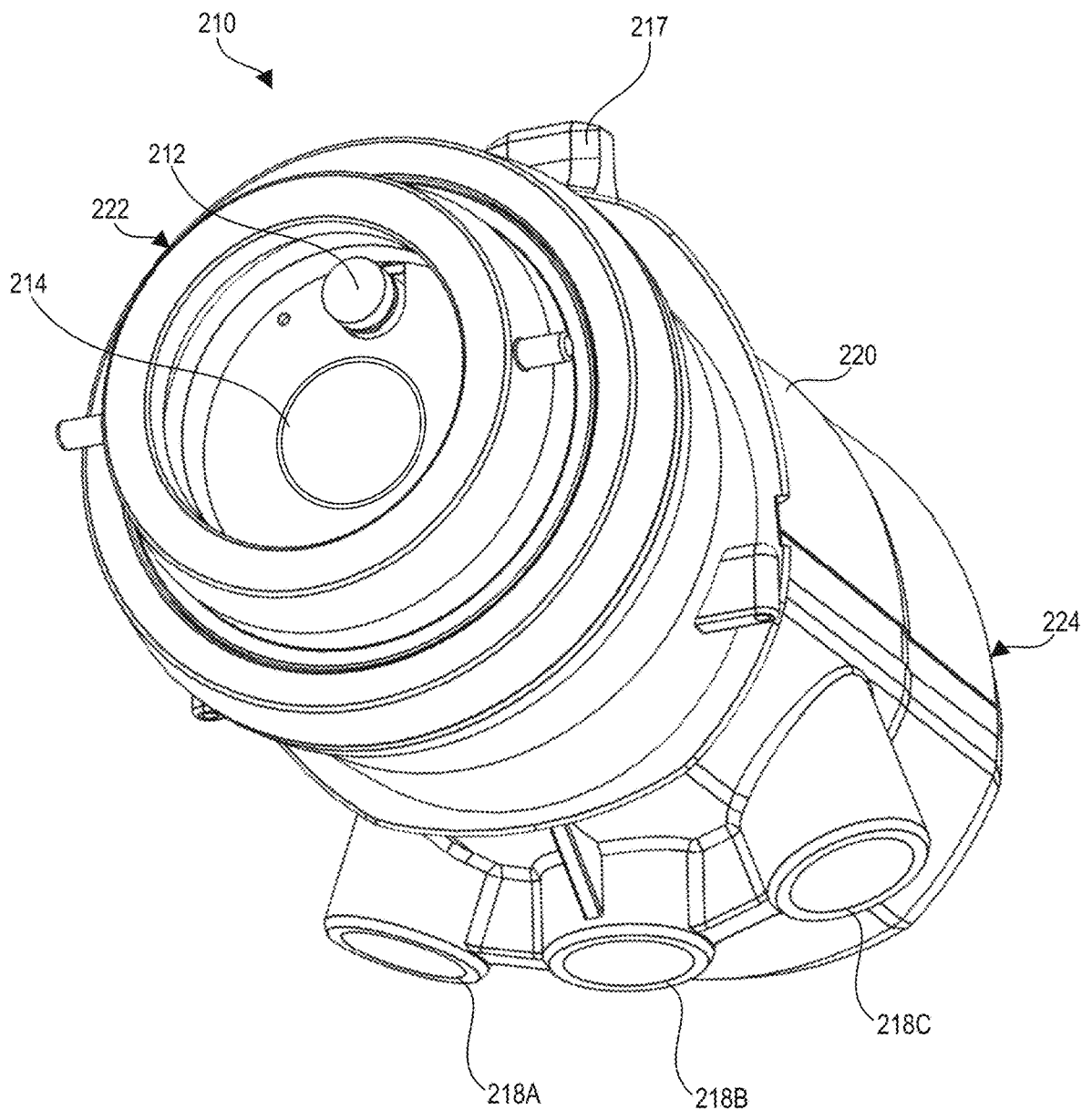
FIG. 2B is an illustration depicting a bottom perspective view of the receiver of FIG. 2A.
Figure 2C:
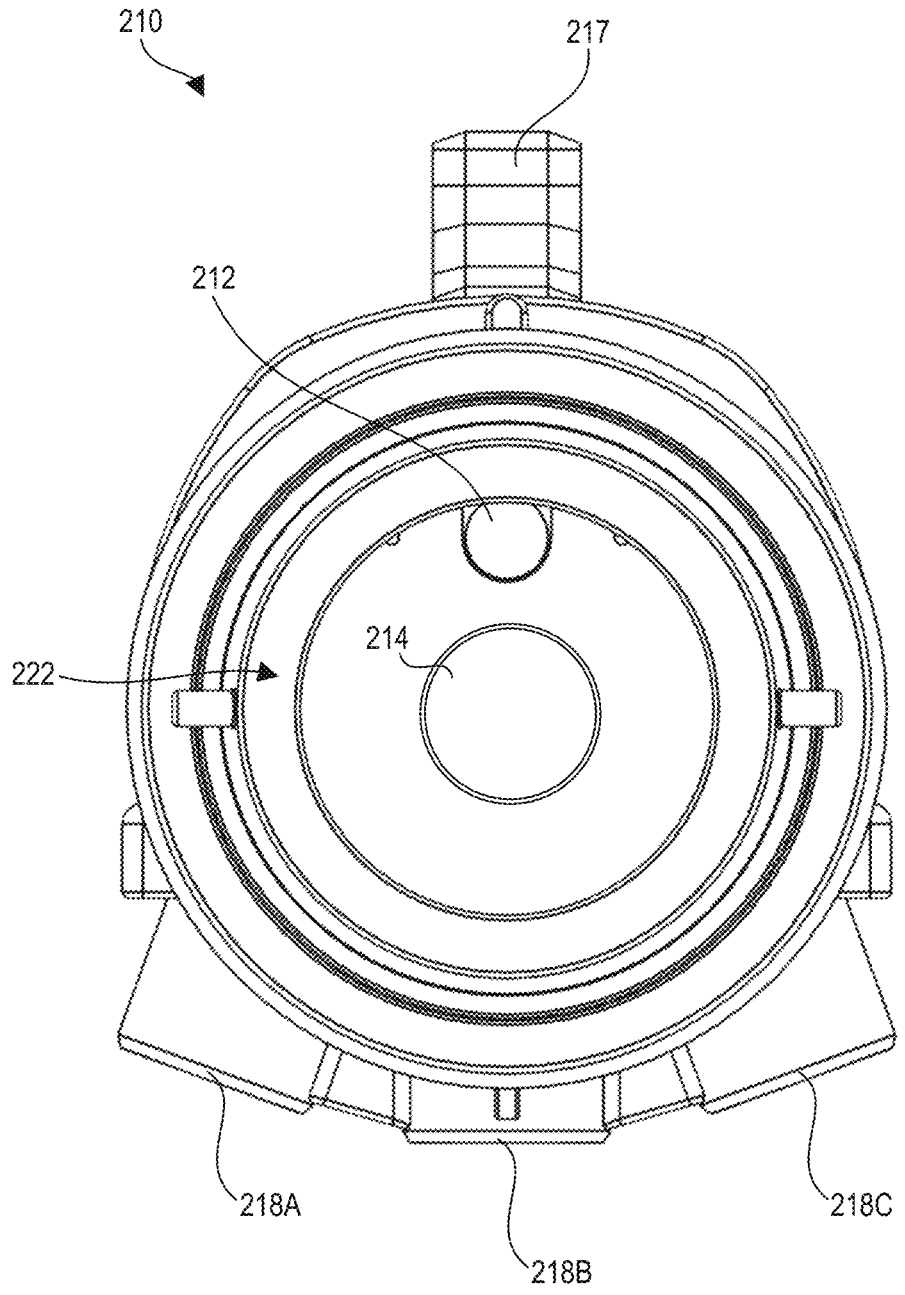
FIG. 2C is an illustration depicting a front view of the receiver of FIGS. 2A-2B.

FIGS. 2A-2C depicts various views of a receiver 210 having an integrated optical sensor 212 that may be used in an open path gas detection system, such as that of FIGS. 1A-1B. The receiver 210 may include a housing 220 having a front end 222 and a rear end 224. The front end 222 may be positioned to face in the direction of a transmitter when the receiver 210 is in use. The optical sensor 212 may be positioned on the front end 222 along with a light sensor 214. The housing 220 may further include one or more support mechanisms 217 which may be used to attach or position the receiver 210. It should be readily appreciated that the housing 220 may include various other structural features to assist in the positioning, attachment, or the calibration and alignment of the receiver 210. Additionally, the housing 220 may further include one or more interfaces 218A, 218B, 218C configured to facilitate the transfer of an electrical communication (e.g., detection signal, optical image signal, electrical power) to an external device. The housing 220 may be formed of any suitable material known in the art, but may be specifically configured to prevent water exposure or other environmental damage to internal components of the receiver 210, and therefore may be designed to operate in inclement weather conditions.

As shown, the optical sensor 212 and the light sensor 214 may be positioned adjacent to each other in close proximity and facing the same direction. In addition to helping to avoid misalignment of the optical sensor 212 relative to the light sensor 214, this arrangement can also help to ensure that the field of view of the optical sensor 212 includes the path of the focused light beam received by the light sensor 214. Furthermore, the optical sensor 212 and the light sensor 214 may be specifically arranged within a recess of the housing 220, as depicted. A transparent element 226 (e.g., a flat glass piece) may be positioned in front of the optical sensor 212 and the light sensor 214, which may help to ensure that neither sensor becomes damaged due to the elements. If, for example, the optical sensor 212 is instead positioned apart from the light sensor 214, event conditions in close proximity to the light sensor 214 may go undetected. For instance, if the optical sensor 212 is instead attached to another part of the receiver housing 220 or positioned as a separate component next to the receiver 210, a fault condition caused by frost on the transparent element 226 may not be determinable from the optical image data. And again, separating the two components risks movement of one relative to the other, which may have an effect on the information that can be obtained from the optical image data. Accordingly, it may be useful to directly integrate the optical sensor 212 into the receiver 210, as shown.

The optical sensor 212 may be specifically configured for each particular open path gas detector application, but may generally include a lens for focusing received light onto an image sensor or film, which then converts the captured light into an electrical signal that may include the optical image data (e.g., photographs, video). The optical sensor 212 may further include an aperture, a shutter, a focusing system, and/or any other component commonly employed in a digital camera. The optical sensor 212 may be configured so that the ISO, aperture, shutter speed, and various other features of the optical sensor 212 may be adjusted. In particular, the focal length, aperture, and field of view of the optical sensor 212 may be particularly adjusted depending on the positioning of the transmitter, as well as the surrounding environment. Each of the optical sensor 212 and the light sensor 214 may include or be connected to associated optical components (e.g., lens, apertures, etc.). The optical sensor 212 may include a moving mechanism configured to move the field of view of the optical sensor by physically adjusting relevant components. In this manner a user may be provided the ability to adjust the viewing angle of the optical sensor 212 within a certain range. Alternatively or additionally, the viewing angle may be adjusted by the moving mechanism automatically by, for instance, receiving a command signal from a processor based on the determination of a pre-defined event (e.g., a change to the detection signal).

The light sensor 214 may include one or more optical components configured to capture and focus the beam of focused light emitted by the transmitter, as well as a photodetector configured to thereafter receive the focused light and produce an electrical signal (i.e., detection signal) proportional to the intensity of the received focused light. The detection signal may be further amplified, if necessary, or otherwise conditioned to reduce noise, thereby ensuring accurate and reliable detection. A skilled artisan will appreciate that the present techniques may further utilize various light sensor arrangements and techniques known in the art.

Figure 3:
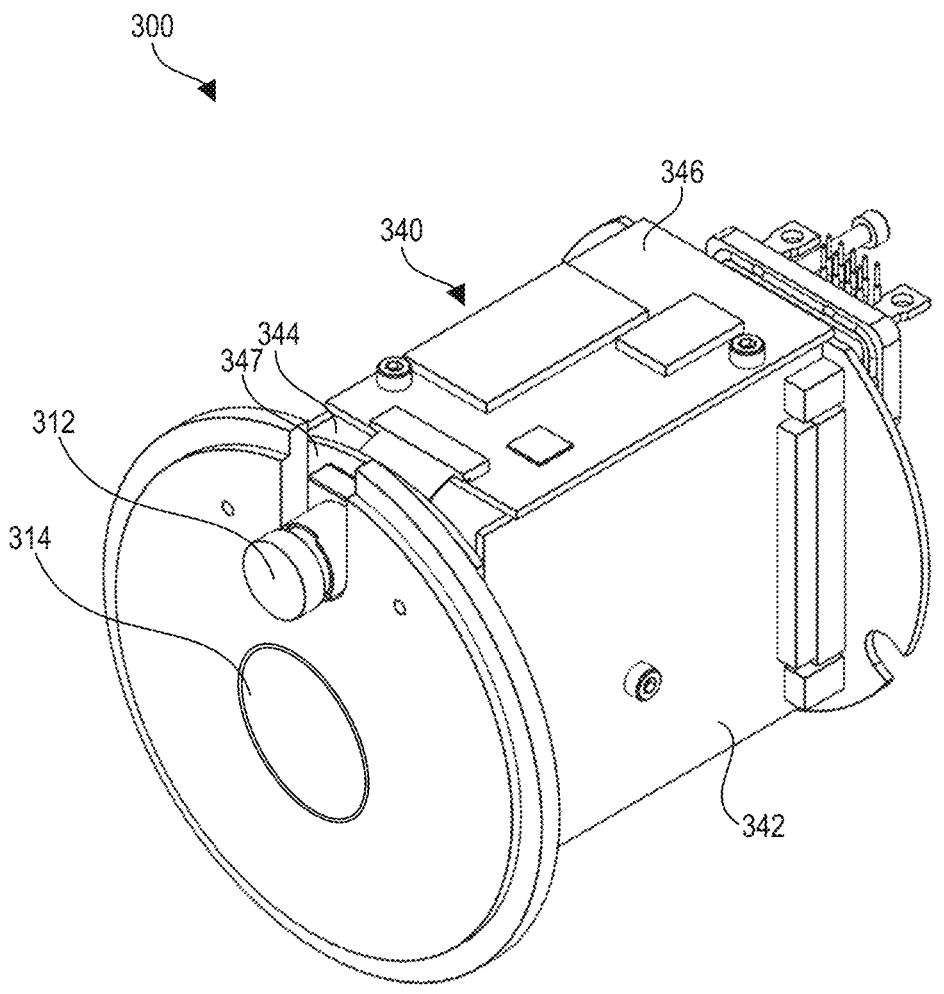
FIG. 3 is an illustration depicting various internal components of a receiver to be used in an open path gas detection system, including a light sensor, an optical sensor, and an electronics assembly.

FIG. 3 depicts various internal components 300 of a receiver to be used in an open path gas detection system, including an optical sensor 312, a light sensor 314, and an internal electronics assembly 340. As shown, the internal electronics assembly 340 may include a first printed circuit board (PCB) 342, a second PCB 344, a third PCB 346, and a fourth PCB 347, one or more of which may be in electrical communication with the optical sensor 312 and/or the light sensor 314.

Figure 4:
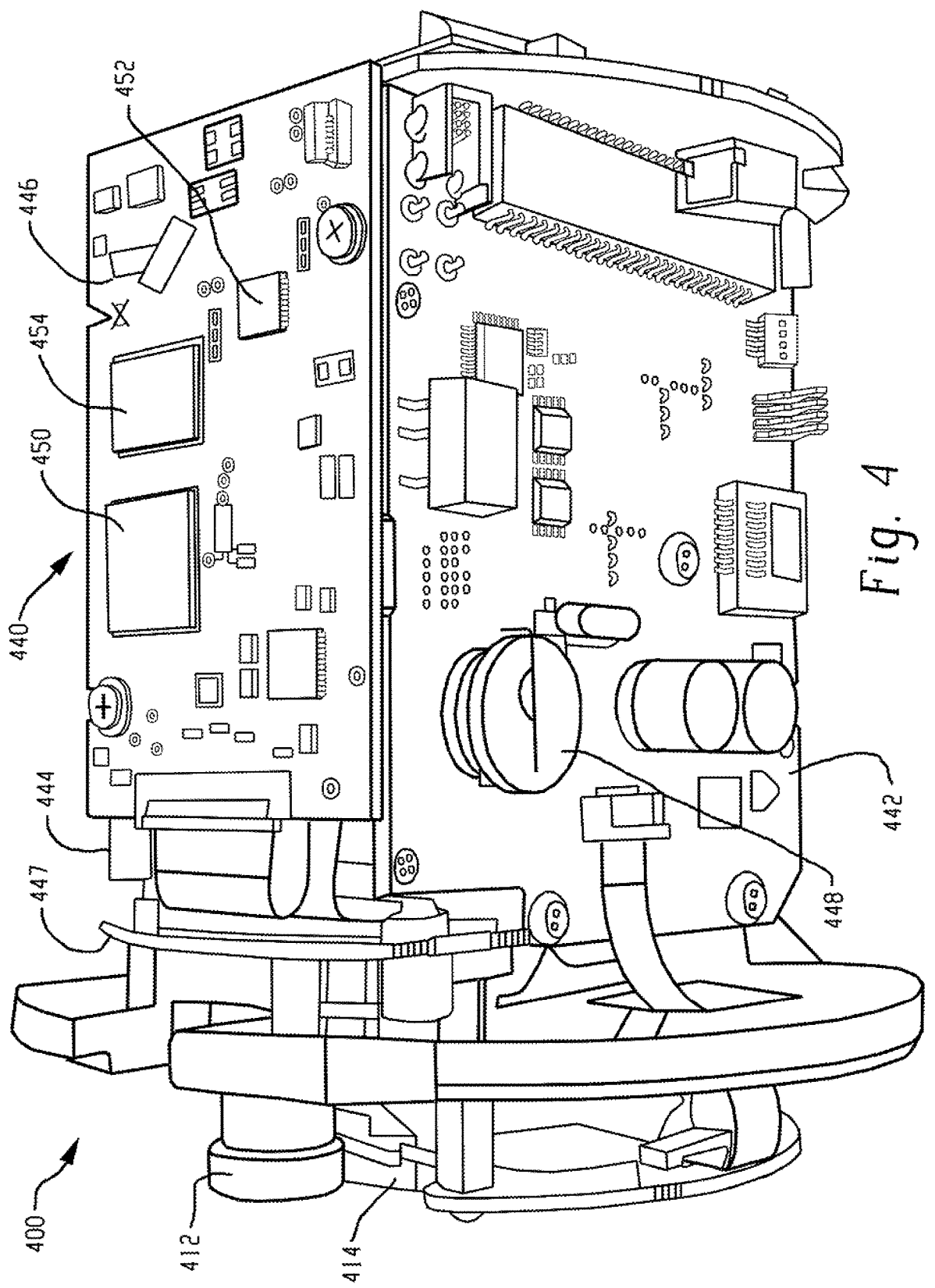
FIG. 4 is a representation depicting a various internal components of a receiver to be used in an open path gas detection system, including a light sensor, an optical sensor, and an electronics assembly.

Similar to FIG. 3, the representation in FIG. 4 depicts various internal components 400 of a receiver to be used in an open path gas detection system, including an optical sensor 412, a light sensor 414, and an internal electronics assembly 440, which may include a first PCB 442, a second PCB 444, a third PCB 446, and a fourth PCB 447, one or more of which may be in electrical communication with the optical sensor 412 and/or the light sensor 414. As shown, the electronics assembly 440 may include or be in electrical communication with various components of the receiver, including but not limited to one or more batteries 448, one or more processors 450, one or more communications units 452, and one or more memory units 454. One of the PCBs 442, 444, 446, 447 or a subsection thereof, may be specifically configured to interact and control the optical sensor 412. For instance, the fourth PCB 447 may be configured to receive and process the optical image data from the optical sensor 412 as well as provide various control signals to the optical sensor 412 (e.g., command to turn off, etc.).

As previously described, the electronics assembly 440 may include both a memory buffer and a persistent memory area. The memory buffer may be configured to receive and temporarily store the optical image data, and to transfer the optical image data to the persistent memory area upon receipt of a transfer command. The memory buffer and the persistent memory area may be contained within the same component of the electronic assembly 440 (e.g., the depicted memory unit 454), or they may be provided as separate components. The memory buffer may be further configured to delete the optical image data after a predefined amount of time (e.g., 1 minute) unless a transfer command is provided. In this manner, absent a transfer command, optical image data that is continuously received may be deleted so as avoid unnecessary storage of optical image data over time. The predefined amount of time that the memory buffer is configured to store the optical image data prior to deleting may be selected to have a minimum length (e.g., at least 10 seconds, at least 30 seconds, at least 1 minute, etc.) so that the optical image data preceding the transfer command may provide a user sufficient context to evaluate the conditions that lead up to the event condition (e.g., enough time to watch a vehicle drive up and block the focused light). Accordingly, after the optical image data has been transferred from the memory buffer, a user may access the optical image data stored in the persistent memory area, which may provide a more-permanent memory storage function, at a later point in time in order to evaluate the status of the open path gas detector.

The processor 450 may be configured to continuously receive the optical image data stored in the memory buffer and to continuously determine if an event condition has occurred and a transfer command should be provided. The transfer command may be provided by the electronic assembly 440 in a number of circumstances (i.e., event conditions). For instance, if the detection signal received from the light sensor 414 indicates a fault condition (e.g., blocked or misaligned signal) or a signal change below or above a predefined threshold value or rate of change, the electronic assembly 440 may be configured to provide (e.g., via the processor 450) the transfer command to the memory buffer. Additionally, the electronic assembly 440 may be configured to provide the transfer command upon receiving a request from a user, or when the receiver initiates or completes an action of interest, such as a calibration, commissioning, or system test. Further yet, the processor 450 may be configured to analyze the optical image data being temporarily stored in the memory buffer and to provide the transfer command to the memory buffer based on the optical image data. For example, the processor 450 may be configured to identify if an event condition has occurred (e.g., bird blocking pathway of focused light, misalignment of a transmitter, etc.) based either solely on the optical image data or in combination with the detection signal.

When analyzing the optical image data in order to determine if a transfer command is necessary, the processor 450 may rely on image classification to identify known objects or patterns in the optical image data. For instance, the processor 450 may rely on an image classification model, which may utilize machine learning algorithms. The image classification model may be particularly trained to identify event conditions common to open path gas detectors, including common weather issues (e.g., fog, rain, frost) or objects known to commonly enter the pathway of the focused light emitted from the transmitter (e.g., birds, operators, vehicles, etc.). The processor 450 may be configured to consider the proximity of a recognized object to the focused light pathway and its direction of travel when considering providing a transfer command. For example, an operator walking within the field of view of the optical sensor 412 but not in close proximity to the focused light pathway may be determined to be insufficient to warrant a transfer command.

The processor 450 described herein may be configured to identify the transmitter within the optical image data. Because of the large distance between the transmitter and the receiver, this identification will not always be straightforward. In order to help facilitate identification of the transmitter, the transmitter device may itself include a known identifier, such as a known color or pattern. For example, the transmitter may specifically include a light source configured to produce a predetermined light emission (e.g. a patterned light signal) and the processor 450 may be configured recognize the light emission and thereby identify the transmitter within the optical image data. The processor 450 may use the identification of the transmitter to determine a misalignment or blockage of the focused light pathway. For instance, if the location of the stationary transmitter shifts within the field of view of the optical sensor 412, it may be determined that alignment of the receiver has been altered.

Once the memory buffer receives the transfer command, it may be configured to provide the current optical image data being stored as well as to continuously provide optical image data to the persistent memory area for a predefined period of time (e.g., 1 minute), or until a stop-transfer command is provided. A stop-transfer command may be provided based on, for example, the detection signal (e.g., upon return to a normal value), receipt of a request from a user to stop the transfer, expiration of a predefined period of time following initiation of transfer, and/or the optical image data (e.g., an identified object leaves the field of view).

Figure 5:
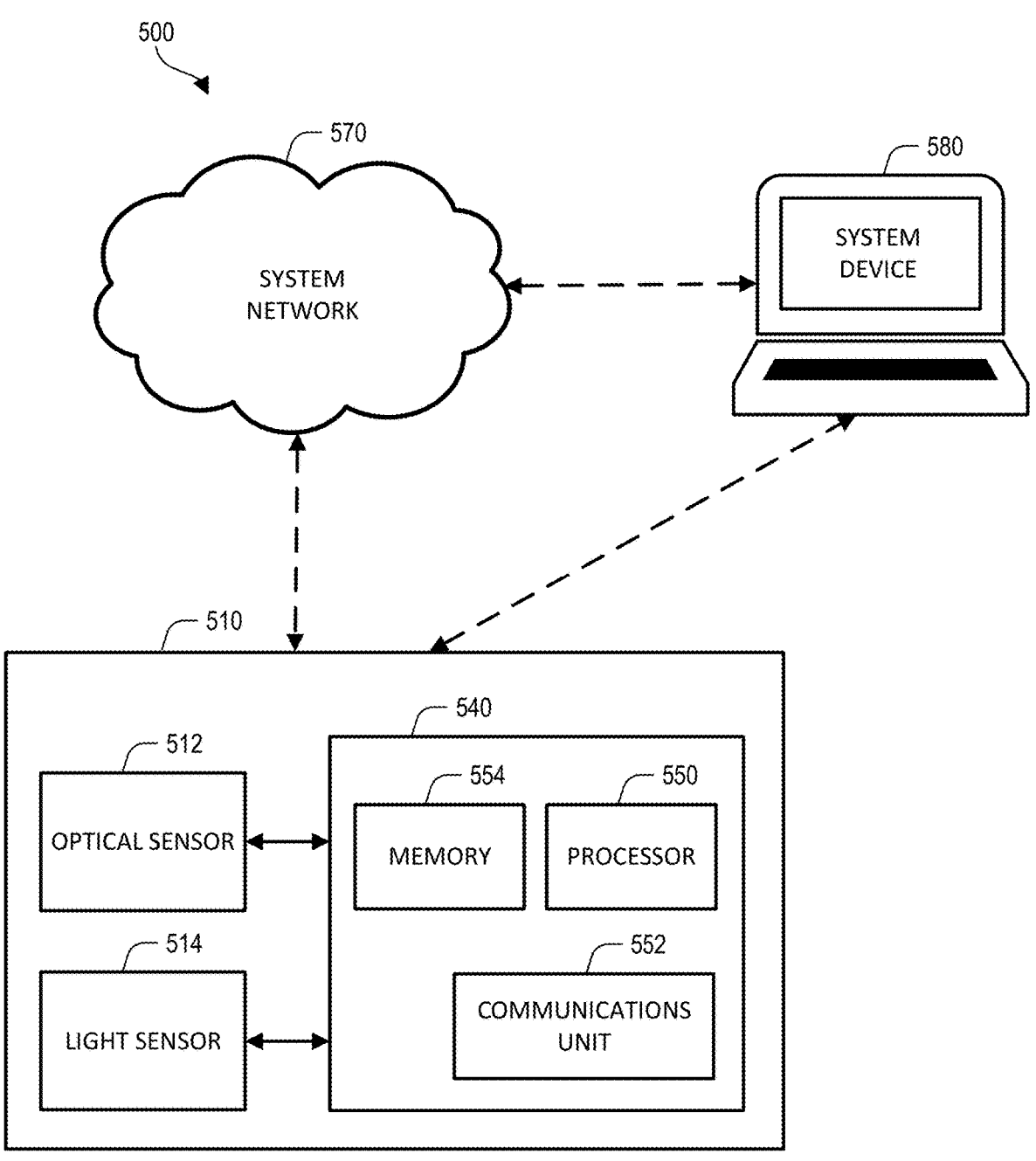
FIG. 5 is a diagram depicting a receiver to be used in an open path gas detection system interacting with a system network and a system device.

FIG. 5 is a diagram depicting a receiver 510 to be used in an open path gas detection system 500 interacting with a system network 570 and a system device 580. As previously described, the receiver 510 may include an optical sensor 512, a light sensor 514, and an electronic assembly 540 which may include a memory 554, a processor 550, and a communications unit 552. The receiver 510 may be configured to provide information to the system network 570 as well as system devices 580 via either wireless or wired connection. The information provided may include, at least, information relating to the detection signal and the optical image data. For instance, the receiver 510 may provide optical image data in the form of a video to one or more servers of the system network 570, and this information may then be accessed and viewed on a system device 580 by a user. The information obtained from the optical image data may be provided to the user in one or more different ways, including but not limited to video, photographs, text (e.g., "bird identified"), and/or a modified video (e.g., including a graphical overlay).

The system device 580 may include various device forms, including but not limited to, computers, cell phones, operator workstations, alarm devices, or other equipment. In some aspects, the system device 580 may be in direct electrical communication with the receiver 510. A user may rely on the system device 580 to provide various command signals to control the receiver 510, including the optical sensor 512. Although various components are described herein as being integrated with the receiver 510, which may be preferable for many applications, it should be appreciated that various components may instead be contained within other system devices. For instance, instead the persistent memory area may be a component of another system device (e.g., server). Likewise, another processor may be configured to analyze the optical image data from within a system device.

Figure 6:
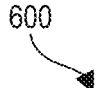
FIG. 6 is an illustration depicting example optical image data with a graphical overlay that could be obtained from a receiver with an integrated optical sensor and provided to a user.
Figure 6:
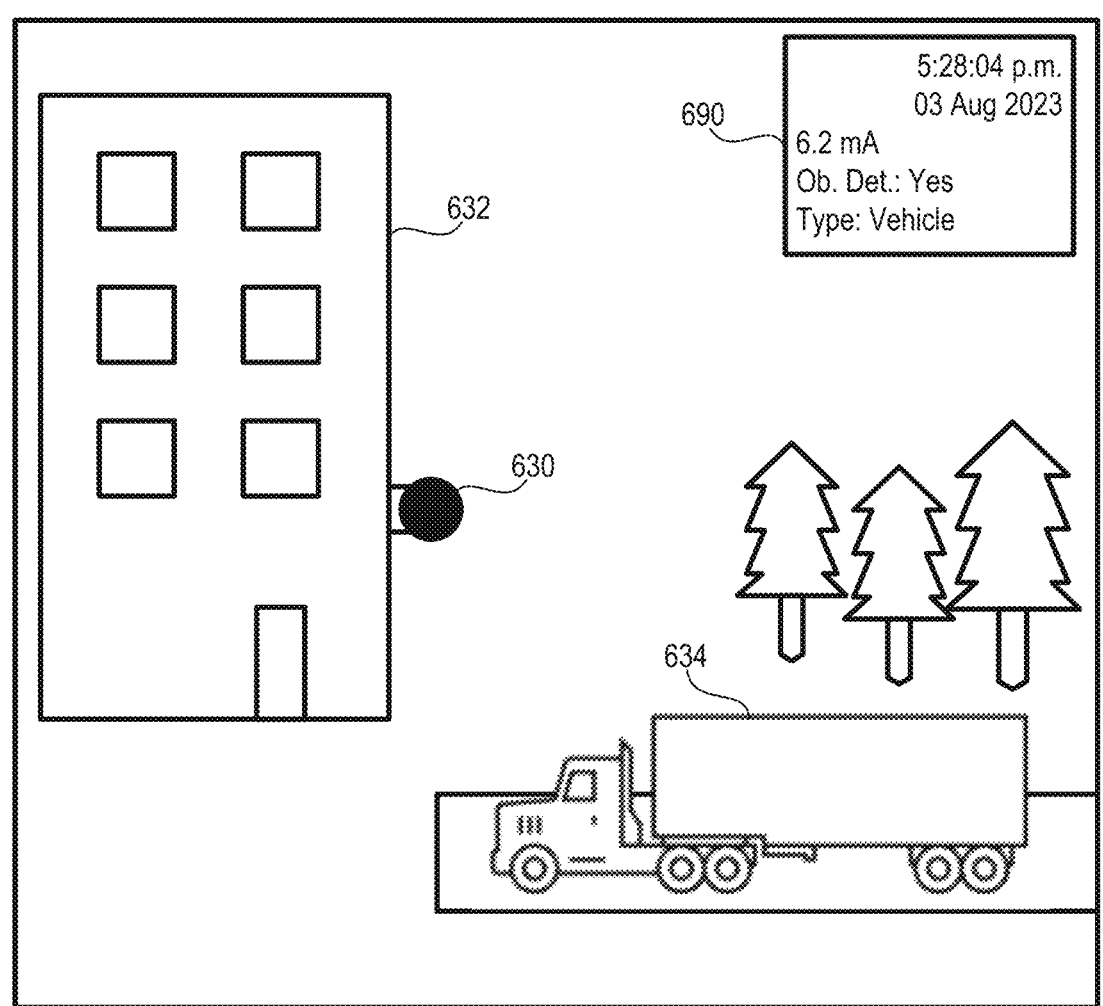

FIG. 6 depicts example optical image data 600 which has been modified to include a graphical overlay 690 that could be obtained from a receiver with an integrated optical sensor and provided to a user. As shown, the example optical image data includes a transmitter 630 positioned on a structure 632. The transmitter 630 may be configured to provide a beam of focused light to the receiver. In this depiction, an object of interest 634, namely a parked vehicle, has entered the field of view of the optical sensor.

As shown, the graphical overlay 690 may include additional information to be reviewed by a user, including a time-and-date stamp, the detection signal value, an indication of whether an object of interest has been identified by the receiver, and the type of object of interest that has been identified. It should readily be appreciated that alternate information may be included and alternate forms of presentation besides graphical overlays may be used, including unique identifiers to distinguish one receiver from another. The receiver may be configured to modify the optical image data 600 by, for example, directly labeling or otherwise emphasizing the identified object of interest 634, the transmitter 630, and/or other objects within the field of the view of the optical sensor (e.g., by placing a colored box around the identified object). Any modification to the optical image data 600 may occur either prior to the optical image data 600 being transferred to the persistent memory area or prior to being provided to a user accessing a system device.

Furthermore, some of the information produced by the receiver may be provided to a user separate from the optical image data 600. The receiver may be configured to provide information to the user that allows them to determine whether the optical image data 600 needs to be reviewed. For instance, the receiver may be configured to provide identity of an object of interest and an indication of whether the object of interest has been resolved (i.e., whether it is still potentially having an effect, or at risk of having an effect, on the detection signal). As one example, if a bird flies into the pathway of the focused light, the receiver may be configured to provide the optical image data to a system device along with a preliminary word alert that specifies that a bird was identified and is no longer in the field of view (e.g., "Ob. Det.: Bird, No Longer Present"). A user may then choose whether it is necessary to open and view the optical image data file.

FIG. 7 depicts a method 700 of gas detection in accordance with various aspects of the present disclosure. At 702, a beam of focused light may be received. At 704, a detection signal containing information regarding the gas within the path of the focused light may be produced based on the received focused light. At 706, optical image data may be captured, wherein the field of view of the optical image data includes the path of the focused light. At 708, the method 700 may include determining whether an event condition has occurred based on the optical image data. An event condition may specifically be an event likely to have an effect on the detection signal. The event condition may be, for example, the appearance of a predefined object of interest within the field of view of the optical sensor or the misalignment of the receiver relative to the path of the focused light.

Although the optical sensor is predominantly described as being included within the receiver of the gas detection system throughout the present disclosure, it should be readily appreciated that the optical sensor may instead be positioned within the transmitter. For example, the optical sensor may be located in the transmitter and function in a similar manner by receiving the transfer signal from the receiver unit via a communication interface or from a user control unit.

While the disclosure has been described in detail and with reference to specific embodiments thereof, it will be apparent to one skilled in the art that various changes and modifications can be made therein without departing from the spirit of the embodiments. Thus, it is intended that the present disclosure cover the modifications and variations of this disclosure provided they come within the scope of the appended claims and their equivalents.

It is claimed:

1. A gas detection system comprising:
    a receiver including:
        a light sensor configured to receive a beam of focused light generated by a transmitter and to produce a detection signal containing information regarding the gas within the path of the focused light;
        an optical sensor configured to continuously capture optical image data, wherein the field of view of the optical sensor includes the path of the beam of focused light; and
        an electronic assembly including a memory buffer and a persistent memory area, wherein the memory buffer is configured to:
        receive and temporarily store the optical image data;
        receive a transfer command based on an analysis of the optical image data; and
        transfer the optical image data to the persistent memory area upon receipt of the transfer command,
            wherein the electronic assembly is configured to provide a stop-transfer command to the memory buffer based on the optical image data.

2. The gas detection system of claim 1, wherein the stop-transfer command is provided based on the detection signal.

3. The gas detection system of claim 1, wherein the stop-transfer command is provided based on receipt of a request from the user.

4. The gas detection system of claim 1, wherein the stop-transfer command is provided based on the expiration of a predefined period of time following initiation of a transfer.

5. The gas detection system of claim 1, wherein the stop-transfer command is provided based on an analysis of the optical image data.

6. A gas detection system comprising:
a receiver including:
    a light sensor configured to receive a beam of focused light generated by a transmitter and to produce a detection signal containing information regarding the gas within the path of the focused light;
    an optical sensor configured to capture optical image data, wherein the field of view of the optical sensor includes the path of the focused light; and
    an electronic assembly including a processor configured to:
        receive the optical image data;
        identify a predefined object of interest;
        determine that a first event condition has occurred when the predefined object of interest is identified in the optical image data;
        transfer the optical image data over a network when the first event condition has occurred; and
        halt the transfer of the optical image data over the network when a second event condition has occurred.

7. The gas detection system of claim 6, wherein the processor is configured to continuously receive the optical image data and to continuously determine if the first event condition has occurred based on the optical image data.

8. The gas detection system of claim 6, wherein the second event condition is the object of interest is no longer identified in the optical image data.

9. The gas detection system of claim 6, wherein the second event condition is the expiration of a predefined period of time.

10. The gas detection system of claim 6, wherein the second event condition is the receipt of a user stop-transfer command.

11. A gas detection system comprising:
a receiver including:

a light sensor configured to receive a beam of focused light generated by a transmitter and to produce a detection signal containing information regarding the gas within the path of the focused light;
    an optical sensor configured to capture optical image data, wherein the field of view of the optical sensor includes the path of the focused light; and
    an electronic assembly including a processor configured to:
        attempt to identify the transmitter in the optical image data;
        transfer the optical image data over a network based on a failure to identify the transmitter in the optical image data indicating misalignment.

12. The gas detection system of claim 11, wherein the electronic assembly includes a memory buffer configured to receive and temporarily store the optical image data and to delete the optical image data after a predefined amount of time unless a transfer command is received.

13. The gas detection system of claim 11, wherein the electronic assembly is configured to modify the optical image data transferred over the network.

14. The gas detection system of claim 13, wherein the optical image data is modified to include information obtained from the detection signal.

15. The gas detection system of claim 14, wherein the optical image data is modified to include a signal strength value of the detection signal.

16. The gas detection system of claim 13, wherein the optical image data is modified by labeling an identified object of interest.

17. The gas detection system of claim 11, wherein the light sensor is positioned adjacent to the optical sensor within a housing of the receiver, and wherein a transparent component is positioned adjacent to both sensors along the path of the focused light.

18. The gas detection system of claim 11, wherein the optical image data includes a video file.

* * * * *